United States Patent [19]

Yasunaga et al.

[11] Patent Number: 4,958,513
[45] Date of Patent: Sep. 25, 1990

[54] GAS DETECTING DEVICE

[75] Inventors: Susumu Yasunaga, Osaka; Kazuo Okino, Hyoogo, both of Japan

[73] Assignee: Figaro Engineering, Inc., Osaka, Japan

[21] Appl. No.: 305,172

[22] Filed: Feb. 2, 1989

[30] Foreign Application Priority Data

Feb. 4, 1988 [JP] Japan .................................. 63-25302

[51] Int. Cl.$^5$ ............................................ G01N 27/00
[52] U.S. Cl. ...................................... 73/23.2; 98/2.01
[58] Field of Search ...................... 98/2.01; 165/16, 43; 73/23, 27; 422/98

[56] References Cited

U.S. PATENT DOCUMENTS

| 4,167,925 | 9/1979 | Hosaka et al. | 123/489 |
| 4,437,391 | 3/1984 | Eguchi et al. | 98/2.01 |
| 4,458,583 | 7/1984 | Fukui et al. | 98/2.01 |
| 4,478,049 | 10/1984 | Fukui et al. | 98/2.01 |

FOREIGN PATENT DOCUMENTS

| 56-131412A | 3/1980 | Japan . |
| 6027849A | 7/1983 | Japan . |
| WO/0270 | 4/1988 | PCT Int'l Appl. . |

Primary Examiner—Hezron E. Williams
Attorney, Agent, or Firm—Kerkam, Stowell, Kondracki & Clarke

[57] ABSTRACT

When the output of a gas sensor is approximately constant, the sensor output is stored as a reference output. Evolution of a gas is detected from variations in the sensor output from the stored reference output. The sensor output which is constant is detected by establishing that the difference between a maximum and a minimum of sensor output in a predetermined section is not greater than a specified value.

4 Claims, 8 Drawing Sheets

GAS DETECTING DEVICE

FIELD OF THE INVENTION

The present invention relates to devices for detecting a gas from relative variations in the output of a gas sensor. The gas detecting devices of the invention are used, for example, for detecting air pollution or gas leaks.

TERMINOLOGY

The term "gas sensor output" used herein is to be so interpreted that the output decreases when the ambient atmosphere is cleaned and increases when the atmosphere is polluted. Since there are cases wherein reverse results are obtained depending on the type of sensor or signal processing method used, it is likely that the magnitude of the sensor output referred to herein will not correspond to the magnitude of the actual sensor output.

PRIOR ART

Examined Japanese Patent Publication No. SHO 59-39,330 (Unexamined Japanese Patent Publication No. SHO 56-131,412) and U.S. Pat. No. 4,352,321 disclose systems for automatically controlling air conditioners with use of a gas sensor. These systems have the following features.

(1) The reference output is renewed at an interval of about 1 minute. The output of the sensor at the time of renewal is used as the reference output.

(2) Air pollution is detected from the variation in the sensor output from the reference output to operate a ventilator, air cleaner or like air-conditioning load.

(3) Renewal of the reference output is prohibited during the operation of the air-conditioning load to avoid the use of a sensor output corresponding to polluted atmosphere as the reference output.

(4) The operation of the load is discontinued when the sensor output decreases owing to the operation.

The first advantage of these systems is that the influences of variations in the sensor characteristics with time and of variations in temperature and humidity can be compensated for automatically and that there is no need to adjust sensors individually. Second, the systems have the advantage that air pollution is detectable from a marked increase in the concentration of gas free of the influence of the gas which is present in the ambient atmosphere at all times.

However, the meaning of the reference output read at the predetermined interval is ambiguous. Especially it is difficult to detect atmospheric pollution which proceeds moderately. Furthermore, it is impossible to control the air conditioner if the gas concentration does not decrease despite the operation of the air-conditioning load. For example, in the case of the air cleaner which is intended primarily to remove smoke but is not adapted to remove gases effectively, the air cleaner, even if operated, is unable to greatly reduce the gas concentration although smoke is thereby removal.

Other related prior art includes the following. U.S. Pat. No. 4,437,391 discloses detection of gas using a minimum value of sensor output as the reference output. Unexamined Japanese Patent Publication No. SHO 60-27,849 discloses use of a minimum value of sensor output during a period of about 6 hours as the reference output. U.S. Pat. No. 4,458,583 proposes detection of gas from differential values of sensor output. Further U.S. patent application No. 111,465 proposes altering the reference output upon saturation of the sensor output.

SUMMARY OF THE INVENTION

An object of the present invention is to provide a novel method of sampling a reference output of a gas sensor.

Another object of the invention is to provide a gas detecting device adapted to sample a reference output when the gas concentration of the atmosphere is stable.

Another object of the invention is to provide a gas detecting device adapted to sample a reference output when the gas concentration of the atmosphere is stable or decreasing.

According to the present invention, the reference output is sampled when the device detects the output of a gas sensor remaining approximately constant with time. The sensor output which remains constant is detected, for example, by sampling a maximum value and a minimum value of the sensor output in a predetermined section and recognizing that the difference between these values is not greater than a specified value. Instead of directly sampling the maximum and minimum values, the sensor outputs at a plurality of points in a predetermined section may be stored to use the difference between the stored values for the detection. This means an approximate comparison between the maximum and the minimum in the section. The reference output sampling, which is performed when the sensor output remains approximately constant, may alternatively be done when the sensor output is monotonously decreasing so as to cause the reference output to promptly reflect decreasing gas concentration. More specifically, this can be accomplished, for example, by storing the sensor output at a plurality of points in a predetermined section and making linear approximation of the stored output values. When the line obtained has a slope of zero or a negative slope and is closely correlated with the stored output values, a reference output is sampled.

The sensor output which remains approximately constant means that the ambient atmosphere has a constant gas concentration and is stable. The sensor output then affords a reliable reference output when taken as such. For example when a minimum value of sensor output is used as the reference, the reference output is influenced by a decrease in the sensor output due to an accidental cause.

Specific examples of uses of the present device will be discussed. When the device is used for controlling air cleaners, the gas resulting from occurrence of smoke is detected to indirectly detect the smoke. If the sensor output then remains approximately constant, this means that no gas or smoke is produced. When the device is used for motor vehicles for controlling the intake of outside air, the target of detection is air pollution due to a decrease in the distance between vehicles. If the sensor output then remains approximately constant, this means that the distance is great and that the outside air is not polluted with the exhaust gas from preceding vehicles. In the case of detection of gas leaks, the sensor output remaining constant means that there is no leak. In any of these cases, the reference output is sampled on condition that the sensor output is substantially constant. It is then possible to compensate for the influences, for example, of variations in the sensor characteristics with time and of the temperature or humidity dependence of the sensor.

BRIEF DESCRIPTION OF THE DRAWINGS

FIG. 1 show characteristics of an embodiment, FIG. 1 (1) being a characteristics diagram representing the concentration of smoke, FIG. 1 (2) being a characteristics diagram representing the output of a gas sensor, and FIG. 1 (3) being an operation characteristics diagram of an air cleaner;

FIGS. 2 (A) to (E) are characteristics diagrams showing different methods of sampling a reference output for use in the embodiment;

EMBODIMENTS

EMBODIMENT 1

FIGS. 1 to 4 show a first embodiment. It is assumed that this embodiment is used for controlling an air cleaner.

Figure 1A:
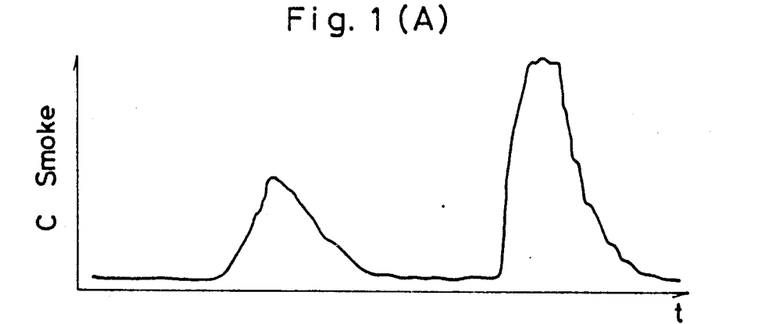
Figure 1B:
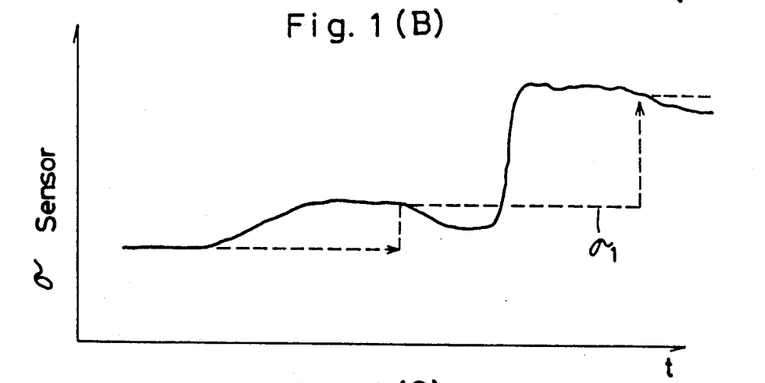
Figure 1C:
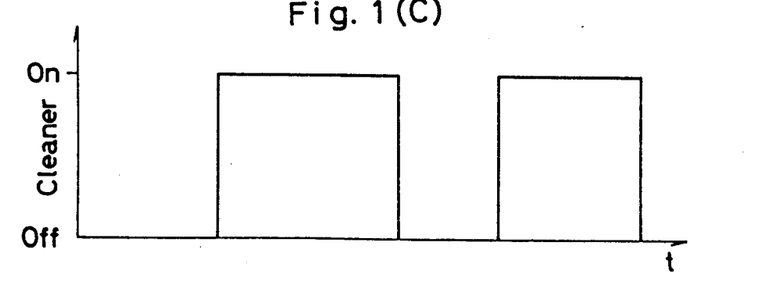

FIG. 1 shows operation waveforms of the embodiment; the concentration of smoke is shown in (1), the output (electric conductivity $\sigma$) of a sensor in (2) and the operation of an air cleaner in (3). An n-type metallic oxide semiconductor, such as $SnO_2$, is used for the sensor. Contemplated as the air cleaner is one comprising an electric dust collector and an active carbon or like filter in combination therewith and intended to primarily remove smoke and secondarily remove gases. In this case, the air cleaner is operated upon the evolution of gas involved in the generation of smoke.

The air cleaner, even if operated, will not appreciably lower the concentration of gas, whereas if the air cleaner is controlled with attention directed to the fact that the sensor output is flat, that is, the output remains approximately constant, satisfactory control performance is available. More specifically stated, in the case where the sensor output varies as represented by a solid line in FIG. 1,(2), a reference output $\sigma_1$ is sampled as represented by a broken line in this diagram. The reference output $\sigma_1$ is sampled when it is established that the sensor output remains approximately constant for a period of about 5 to about 30 minutes using a suitable timer or the like.

Reference output sampling conditions will be described with reference to FIGS. 2 (A) to (D). In the case of FIG. 2 (A), the sensor output is sampled at a suitable interval of about 30 seconds to about 5 minutes to obtain sampled values A to F and compare the maximum and minimum of these values. When the difference between the two values is not greater than a specified value, this is interpreted as indicating that the sensor output is approximately constant. In the case of FIG. 2 (B), the sensor output gently increases and is not to be regarded as constant.

Figure 2A:
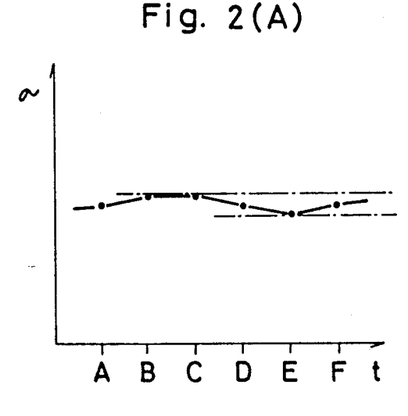
Figure 2B:
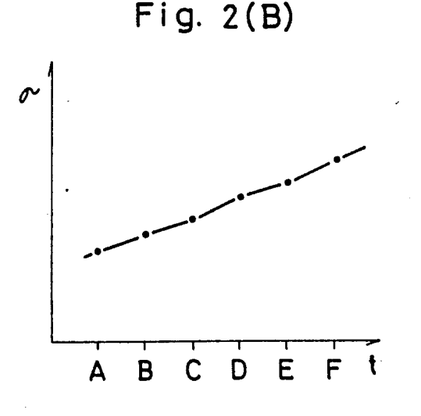
Figure 2C:
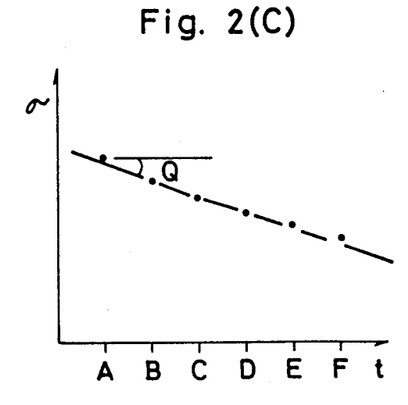

The reference output sampling, which is performed when the sensor output remains constant, may also be done when the sensor output is decreasing. FIG. 2 (C) shows such a case. In this case, linear approximation is made of sampled values A to F, and a reduction in the sensor output is detected from the negative slope of the approximation line obtained. Next, the variance of the sampled values from the approximation line is checked. When the value is not greater than a predetermined value, this indicates that the sensor output is decreasing smoothly or monotonously.

Figure 2D:
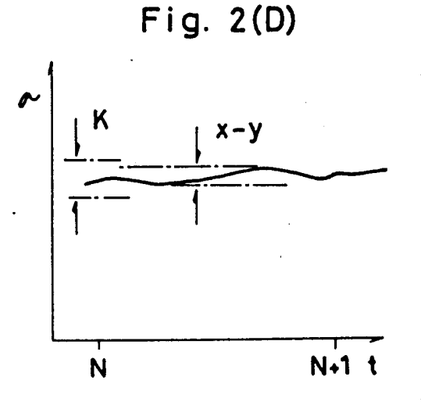

Any desired method is usable for detecting the approximately constant sensor output. In the case of FIG. 2 (D), for example, a timer provides suitably divided sections. A maximum x and a minimum y are sampled in each section (section N is shown). The difference $x-y$, when smaller than a predetermined value K, is interpreted as indicating that the sensor output remains approximately constant. Alternatively, the sensor output may be subjected to analog differentiation to interpret that the output is approximately constant if the differential value is within a specified range. It is also useful to determine that the sensor output is approximately constant, for example, from the following requirement.

$$|A-D|+|B-E|+|C-F| \leq K$$

where A to F are the sensor output values at the respective points of time shown in FIG. 2 (A).

Figure 3:
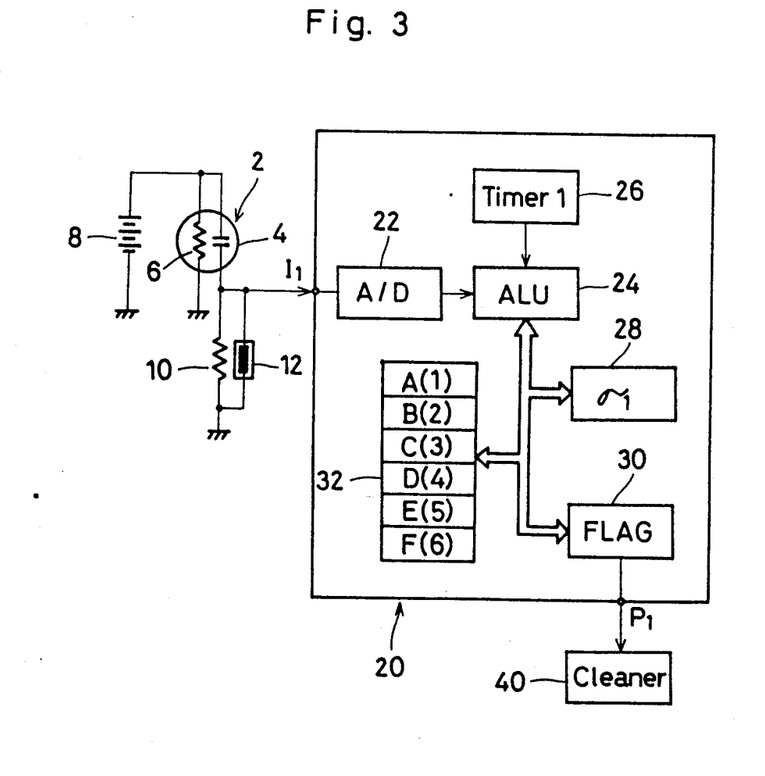
FIG. 3 is a circuit diagram of the embodiment.

With reference to FIG. 3, a circuit will be described which meets the requirement of FIG. 2 (A). The diagram shows a gas sensor 2 comprising $SnO_2$ or like n-type metallic oxide semiconductor 4 which is adapted to be heated by a heater 6. Of course, the gas sensor 2 can be any desired sensor comprising a proton conductor, solid electrolyte such as $ZrO_2$, or the like. Indicated at 8 is a circuit power supply, at 10 a loading resistor for the sensor 2, and at 12 a thermistor for partly compensating for the temperature and humidity dependence of the sensor 2. The thermistor 12 need not always be used.

The circuit further includes a microcomputer 20, A/D converter 22, arithmetic and logic unit 24, timer 26 for setting a time interval of about 5 to about 30 minutes, RAM 28 for storing the reference output $\sigma_1$, and RAM 30 for storing a pollution detection signal (FLAG). A RAM 32 is used for storing sensor output values at points of time A to F dividing the time interval set by the timer 26 into six equal portions. The microcomputer 20 further has a ROM having stored an operation program, an input port $I_1$ and an output port $P_1$. These ports are used for controlling an air cleaner 40.

Figure 4:
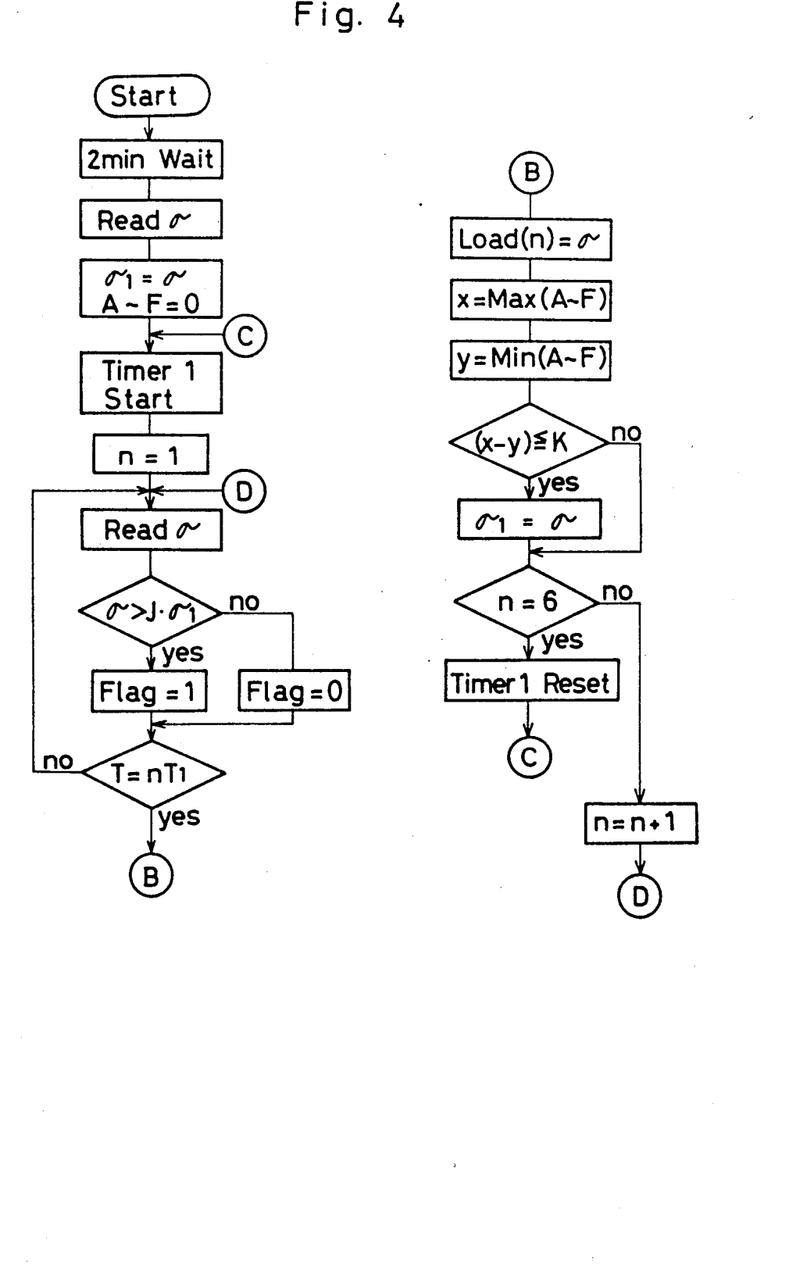
FIG. 4 is an operation flow chart of the embodiment.

The operation of the device will be described with reference to the flow chart of FIG. 4. For example, 2 minutes after the power supply 8 is turned on, the sensor output is read and stored as an initial value of reference output $\sigma_1$. The RAM 32 is set to an initial value of 0. Table 1 below shows the meanings of the symbols used in FIG. 4.

TABLE 1

| Symbol | Meaning |
|---|---|
| $\sigma_1$ | Reference output |
| $\sigma$ | Instantaneous value of sensor output (electric conductivity) |
| A-F | Values stored in RAM 32 |
| n | Number of each of 6 divided sections of timer operation period |
| $T_1$ | 1/6 of timer operation period |
| FLAG | Pollution detection signal |

After initialization, the timer 26 is started, and the time period set by the timer is divided into 6 equal sections. The sensor output is stored in the RAM 32 upon lapse of every divided section. The maximum and the minimum of the values A to F stored in the RAM 32 are represented by x and y, respectively. The difference x−y, when not greater than K, is interpreted as indicating that the sensor output remains approximately constant with time, and the current sensor output is taken as a reference output $\sigma_1$. The value K is, for example, about 1.02 to about 1.08. The sensor output at the time when it is regarded as approximately constant is used as the actual value of reference output. The character n in FIG. 4 refers to the nth of the 6 divided sections of the timer period. The equation Load(n)=$\sigma$ represents an instruction to store the sensor output $\sigma$ at the nth address of the RAM 32. In this way, the reference output is sampled upon detecting the sensor output being approximately constant.

Pollution is detected in the following manner. J times the reference output $\sigma_1$ is used as an operation threshold value for the air cleaner 40. The value J is, for example, about 1.3. The sensor output, when greater than J·$\sigma_1$, is interpreted as indicating pollution. If not greater than J·$\sigma_1$, the output is interpreted as indicating that the ambient atmosphere is clean. In the event of pollution, the signal (FLAG) of the RAM 30 is set to 1, but otherwise, the signal is 0, for the control of the air cleaner 40. Various methods of obtaining the operation threshold value from the reference output $\sigma_1$ are known as disclosed, for example, in the aforementioned Examined Japanese Patent Publication No. SHO 59-39,330, Unexamined Japanese Patent Publication No. SHO 60-27,849, etc.

EMBODIMENT 2

Figure 5A:
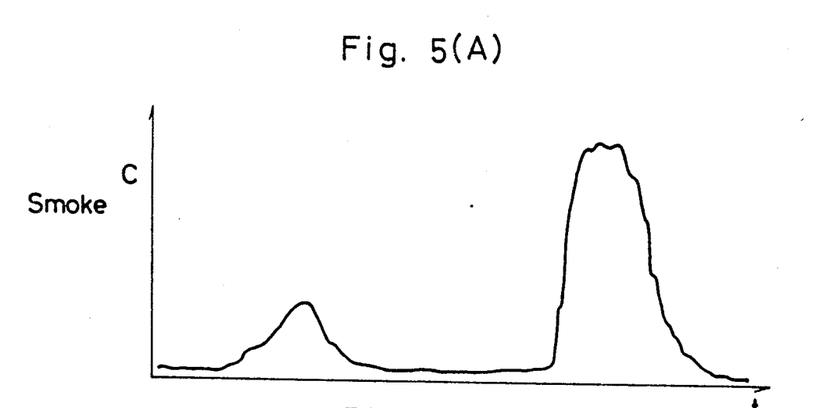
FIG. 5 shows characteristics of a second embodiment, FIG. 5 (1) being a characteristics diagram representing the concentration of smoke, FIG. 5 (2) being a characteristics diagram representing the output of a gas sensor, and FIG. 5 (3) being an operation characteristics diagram of an air cleaner.
Figure 5B:
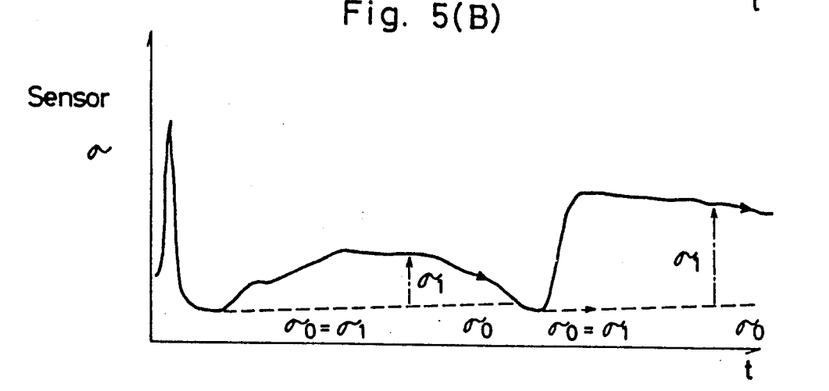
Figure 5C:
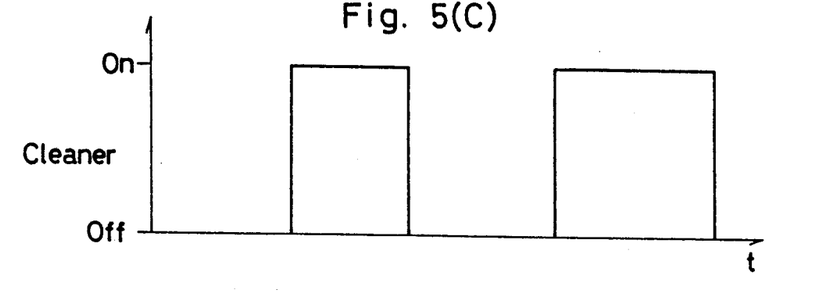

FIG. 5 shows a more complex embodiment. With this embodiment, a sensor output corresponding to a clean atmosphere is stored as a reference output $\sigma_0$, and the two reference outputs $\sigma_0$, $\sigma_1$ are used for control. For example, a minimum value of sensor output is used as the reference output $\sigma_0$. However, lapse of a long period of time after the sampling of the reference output $\sigma_0$ results in lower reliability due to variations in temperature and humidity. Accordingly, the reference output $\sigma_0$ is increased at a rate of about 5 to about 10% every two to six hours. This increase rate is to be in conformity with the rate of increase in the sensor output due to variations in temperature and humidity in a clean atmosphere. When the sensor output does not decrease, the reference output $\sigma_0$ is gradually increased at this rate. When the sensor output lowers below the reference output $\sigma_0$, the actual sensor output is substituted for the reference output $\sigma_0$. When the temperature or humidity rises, the reference output $\sigma_0$ is increased at a rate in conformity therewith, whereas when the temperature or humidity lowers, the output is decreased to a corresponding value after the atmosphere has been cleaned. In this way, the reference output $\sigma_0$ corresponding to clean air is available.

With the present embodiment, the reference output $\sigma_1$ is altered also when the sensor output is monotonously decreasing. Further the renewal of the reference output $\sigma_1$ should be so made that the greater the variation in the reference output for renewal, the longer is the period of time during which the sensor output is to remain stable before the renewal.

Figure 6:
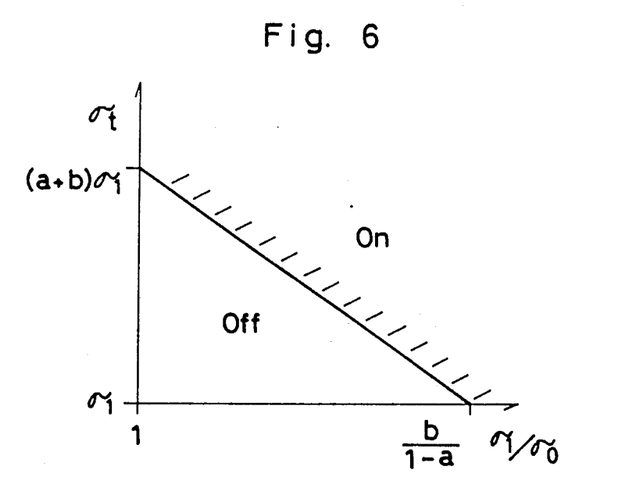
FIG. 6 is a characteristics diagram of the second embodiment showing the operation threshold value of the air cleaner.

FIG. 6 shows the condition involving the combination of the two reference outputs $\sigma_1$ and $\sigma_0$ for setting the operation threshold value $\sigma t$. The threshold value $\sigma t$ is expressed, for example, by:

$$a\sigma_1 + b\sigma_0$$

Generally, the output of the metallic oxide semiconductor gas sensor 2 is not proportional to the gas concentration but is in proportion to the 0.6th to 0.8th power of the gas concentration. Accordingly, if the threshold value is calculated only from the reference output $\sigma_1$, problems will arise. For example, it is assumed that the gas concentration corresponding to the reference output is C, and that the air cleaner 40 is to be operated when the gas concentration increases to C+$\Delta$C. If the operation threshold value is calculated only from $\sigma_1$, the greater the value $\sigma_1$, the greater is $\Delta$C. Further when the influence on the health is considered, it is desired to decrease $\Delta$C as the concentration C increases.

To meet the need, therefore, the reference output $\sigma_0$ is used in combination with the reference output $\sigma_1$ for setting the threshold value. The greater the ratio a/b, the more dependent is the threshold value on $\sigma_1$, while the smaller the ratio a/b, the more dependent is the threshold value on $\sigma_0$. With the present embodiment, a is 0.8 and b is 0.6. This value is equal to $$1.4\sigma_1 - 0.6(\sigma_1 - \sigma_0)$$

The operation threshold value shown in FIG. 6 may be so altered as to approach the abscissa of the diagram when $\sigma_1$ is sufficiently greater than $\sigma_0$. Other desired factor can be involved in the combination of the reference outputs $\sigma_1$ and $\sigma_0$ for setting the threshold value.

Figure 7:
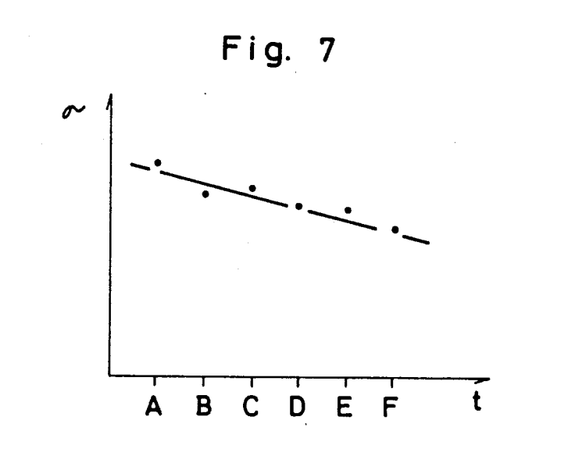
FIG. 7 is a characteristics diagram of the second embodiment showing a method of sampling a reference output.

FIG. 7 shows the condition for sampling the reference output $\sigma_1$. The sensor output is sampled, for example, at an interval of about 1 to about 5 minutes, and the samples values are stored as A to F. Next, the values A and F are compared to determine the slope m of an approximation line representing the values A to F. When F−A is negative or zero, this is interpreted as indicating that the sensor output is constant or is decreasing. If F−A is positive, the difference is interpreted as indicating that the sensor output is increasing, so that the reference output $\sigma_1$ is not renewed. Next, when F−A is negative or zero (m≦0), the variance from the linear approximation is detected. Since the variance is complex to calculate directly, the following value, for example, is used.

$$|A-B+m/5| + |A-C+2m/5| +$$
$$|A-D+3m/5| + |A-E+4m/5| \quad (m=F-A)$$

The reference output $\sigma_1$ is renewed when this value is not greater than a specified value, whereas no renewal is made if otherwise.

Figure 8:
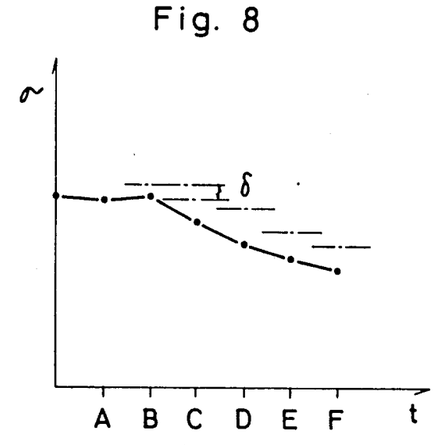
FIG. 8 is a characteristics diagram showing a modified sampling method.

Instead of the sampling condition of FIG. 7, the condition shown in FIG. 8 or the like is usable. Each of the sampled values A to F is compared with the previous two values, i.e. with the smaller of the two, and the smaller value plus an allowance δ is taken as an allowance value. For example, the following calculation is performed.

$$C \leq \text{Min}(A, B) + \delta$$

When this requirement is fufilled six times consecutively, the reference output $\sigma_1$ is renewed.

Figure 9:
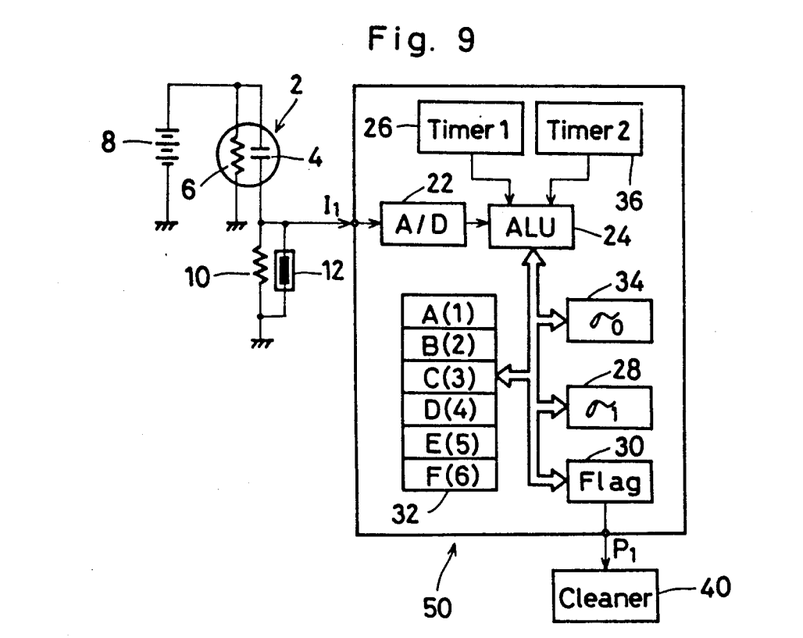
FIG. 9 is a circuit diagram of the second embodiment.
Figure 10:
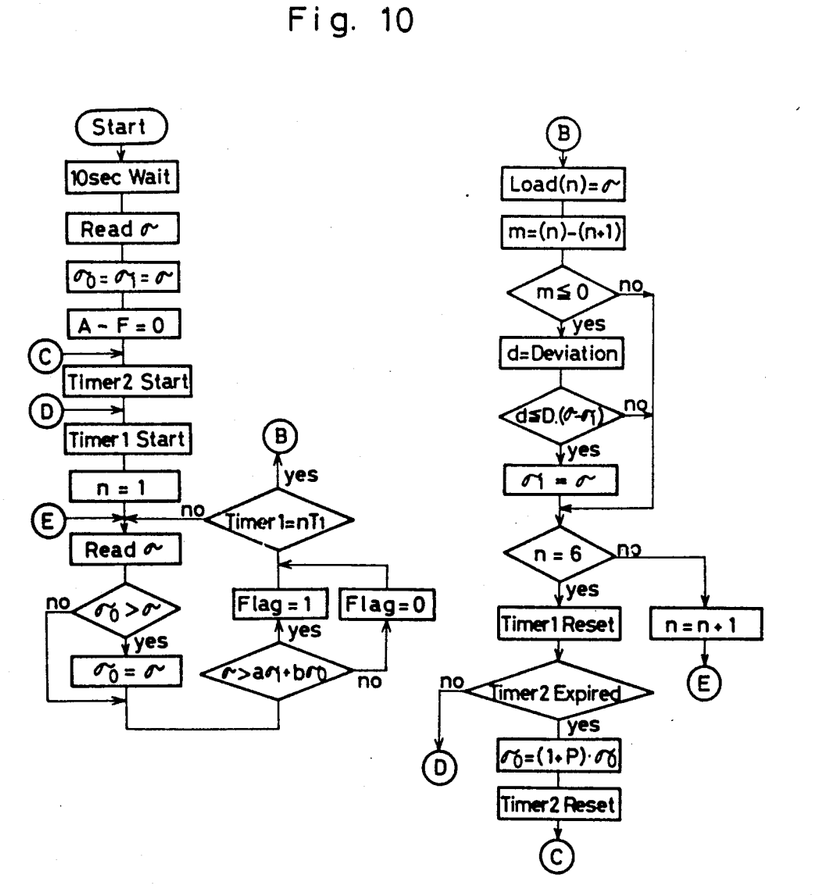
FIG. 10 is an operation flow chart of the second embodiment.

FIG. 9 shows the construction of the circuit of the embodiment, and FIG. 10 the operation program thereof. Throughout the drawings showing the first and second embodiments, like parts are designated by like reference numerals, and like steps execute like processes. Further unless otherwise stated, the same procedures as followed for the first embodiment are to be executed for the present embodiment.

FIG. 9 shows a microcomputer 50, a timer 32 for use in increasing the reference output $\sigma_0$, and a RAM for storing the reference output $\sigma_0$. The microcomputer 50 includes registers and RAM for storing intermediate calculation values.

The operation flow chart of FIG. 10 will now be described. After a waiting period of 10 seconds, the sensor output $\sigma$ is read as initial reference output values $\sigma_0$ and $\sigma_1$. The RAM 32 is set to an initial value of 0 for A to F.

Next, a minimum of sensor output is sampled as the reference output $\sigma_0$, which is then altered using the timer T2 (timer 32) and a constant P. More specifically, when the sensor output $\sigma$ is smaller than $\sigma_0$, $\sigma$ is substituted for $\sigma_0$, and the value is increased at a rate of P upon lapse of every period set by the timer T2. With the present embodiment, the operation period of the timer T2 is 1 hour, and the value P is 3%.

The reference output $\sigma_1$ is sampled by the method of FIG. 7. More specifically, linear approximation is made of the values A to F stored in the RAM 32 to ascertain that the sensor output is constant or is decreasing as the first condition for sampling. Next, the deviation d from the linear approximation is calculated by the foregoing method, and if the value is not greater than $D \cdot (\sigma - \sigma_1)$, the reference output $\sigma_1$ is renewed. D is a constant. When the variation to be made in the reference output $\sigma_1$ is greater, a more stringent condition is employed for renewing the reference output. This results in the advantage that the air cleaner 40 is operated for a longer period of time in the case where the variation in the reference output $\sigma_1$ is great as at the second peak of smoke concentration shown in FIG. 5.

Pollution is detected from whether the sensor output $\sigma$ is above the threshold value of FIG. 6. Upon the detection of pollution, the FLAG signal of RAM 30 is set to 1 for controlling the air cleaner 40.

With reference to FIG. 5, the operation of the device will be described again. A sensor signal corresponding to a clean atmosphere is sampled as the reference output $\sigma_0$. When the sensor output is approximately constant or decreasing, the current sensor output is sampled as the reference output $\sigma_1$. The combination of the two reference outputs $\sigma_0$ and $\sigma_1$ is set as a gas detecting condition. Upon the sensor output reaching a level not lower than the threshold value, the air cleaner 40 is operated to remove the smoke. Although gas remains after the removal of the smoke, the sensor output becomes generally stable unless a gas is evolved. When no gas occurs, this means that no smoke is freshly generated. When the sensor output becomes stabilized, the output remains approximately constant or gradually decreases, so that the reference output $\sigma_1$ is renewed. When renewed, the reference output $\sigma_1$ jumps discretely as seen in FIG. 5 2), the sensor output becomes lower than the operation threshold value, consequently stopping the air cleaner 40. When the variation to be made in the reference output $\sigma_1$ is greater, a more stringent renewal condition is employed. Accordingly, the higher the degree of pollution of the atmosphere, the later is the renewal of the reference output, permitting the air cleaner 40 to operate for a longer period of time.

Although the embodiments have been described with reference to the control of an air cleaner, the invention is useful also for controlling ventilators, deodorizing devices, etc. and for detecting gas leaks, etc. The method of detecting the sensor output which remains approximately constant with time is not limited to those used for the embodiments but can be any method insofar as the constant sensor output can be detected.

What is claimed is:

1. A gas detecting device adapted to detect a gas from relative variations in the output of a gas sensor, the device being characterized in that it comprises:
   means for detecting a sensor output remaining substantially constant with time,
   means for sampling the sensor output at about the time said means produces a signal that the sensor output is substantially constant and storing the sensor output as a reference output, and
   means for detecting the gas from variations in the sensor output relative to the reference output.

2. A gas detecting device as defined in claim 1 wherein the means for detecting a sensor output remaining approximately constant with time serves as means for storing a maximum value and a minimum value of sensor output in a predetermined section and detecting the difference between the maximum and minimum values being not greater than a specified value.

3. A gas detecting device as defined in claim 1 which comprises means for detecting a sensor output monotonously decreasing and wherein the reference output storing means samples the reference output when the sensor output remains approximately constant or is monotonously decreasing with time.

4. A gas detecting device as defined in claim 3 wherein the means for detecting the monotonous decrease in the sensor output serves as means for storing sensor output values at a plurality of points in a predetermined section, making an approximation line by linear approximation of the stored sensor ouput values, and detecting the slope of the approximation line when zero or negative and a difference between the stored output values and the approximation line being an error which is not greater than a predetermined value.

* * * * *